United States Patent [19]

Bergstrom et al.

[11] 3,933,880

[45] Jan. 20, 1976

[54] METHOD OF PREPARING A PLATINUM CATALYST INHIBITOR

[75] Inventors: Floyd A. Bergstrom; Chi-Long Lee; Myron T. Maxson, all of Midland, Mich.

[73] Assignee: Dow Corning Corporation, Midland, Mich.

[22] Filed: Dec. 2, 1974

[21] Appl. No.: 528,961

[52] U.S. Cl. .................. 260/448.2 E; 260/46.5 R; 260/46.5 UA; 260/448.8 R; 252/429 R; 252/431 R
[51] Int. Cl.$^2$..... C07F 7/02; C07F 7/08; C07F 7/18
[58] Field of Search . 260/448.2 E, 448.8 R, 46.5 R, 260/46.5 UA; 252/429 R, 431 R

[56] References Cited
UNITED STATES PATENTS

| | | | |
|---|---|---|---|
| 2,823,218 | 2/1958 | Speier et al. | 260/448.2 E |
| 3,404,169 | 10/1968 | Gaignon et al. | 260/448.2 E |
| 3,419,593 | 12/1968 | Willing | 260/448.2 E |
| 3,453,233 | 7/1969 | Flatt | 260/46.5 UA |
| 3,576,027 | 4/1971 | Fish | 260/448.2 E |
| 3,775,452 | 11/1973 | Karstedt | 260/448.2 E X |
| 3,814,730 | 6/1974 | Karstedt | 260/46.5 UA |

Primary Examiner—Paul F. Shaver
Attorney, Agent, or Firm—Roger H. Borrousch

[57] ABSTRACT

Continuously passing a mixture of an acetylenic alcohol and a siloxane compound having at least three silicon-bonded hydrogen atoms bonded to at least three different silicon atoms in the presence of a platinum catalyst through a heating means wherein the mixture is heated above 100°C. and above the temperature at which the olefinic siloxane compound product is no longer an inhibitor for the reaction and wherein the reactants and products are maintained under sufficient pressure to keep the mixture in a liquid state at least until the mixture has passed through the heating means provides an olefinic siloxane compound which, below 100°C, is an inhibitor for the reaction between the acetylenic alcohol, the siloxane compound having at least three silicon-bonded hydrogen atoms in the presence of platinum.

7 Claims, No Drawings

METHOD OF PREPARING A PLATINUM CATALYST INHIBITOR

BACKGROUND OF THE INVENTION

1. Field of the Invention

This invention relates to a method of preparing a siloxane compound having olefinic unsaturation.

2. Description of the Prior Art

The reaction between compounds having aliphatically unsaturated carbon linkages such as C=C or C≡C with silicon compounds having silicon-bonded hydrogen atoms in the presence of platinum to form new silicon compounds is well known in the art and is known as hydrosilation. A patent by John L. Speier and Donald E. Hook, U.S. Pat. No. 2,823,218, teaches that such reactions can be carried out in the presence of chloroplatinic acid. Speier et al. teach that both olefinic compounds and acetylenic compounds readily react to form new silicon compounds wherein the SiH adds across the unsaturated carbon bonds with a high product yield. Speier et al. also teach that the presence of other substituents in the unsaturated molecule, whether they be functional or entirely inert, does not prohibit the reaction. The unsaturated compounds which undergo reaction are taught as including unsaturated alcohols such as allyl alcohol, methylvinylcarbinol and ethynyldimethylcarbinol. Speier et al. teach that if an unsaturated alcohol is employed, a competing alcoholysis reaction will take place, but the reactants will no longer be those introduced where the source for the SiH is a silane, however, in general this problem does not arise when a siloxane is used as the source of SiH because the siloxanes are relatively inert to any extraneous substituents in the unsaturated reactant.

Speier et al. teach that the reaction temperature can vary over an extremely wide temperature range and optimum temperatures depend upon the concentration of catalyst present and the nature of the reactants. Temperatures suggested range from 0°C. to below 300°C. The temperature should be such that at least one of the reactants or a portion of the reaction mixture is in a mobile stage, liquid or gaseous and the maximum temperature is determined only by the stability of the reactants and the operator's desire to avoid decomposition products.

Speier et al. teach that the reaction time is variable and depends upon the reactants, reaction temperature and catalyst concentration among other things. Contact times of greater than 16 or 17 hours do no harm unless an extremely elevated temperature is employed, however, many reactants give a practically quantitative yield with contact times of 30 minutes or less and often an excellent yield can be obtained as soon as the exothermic reaction has begun which may be a matter of seconds. Speier et al. also teach that the reaction can be carried out at atmospheric, subatmospheric or super-atmospheric pressures. The choice of conditions is a matter of logic based upon the nature of the reactants and the equipment available where nonvolatile reactants are adaptable to being heated at atmospheric pressure with or without reflux and gaseous reactants at ordinary temperatures are preferably reacted at substantially constant volume under autogenous or induced pressure wherein the best results are obtained by maintaining at least a portion of the reactants in the liquid phase.

Speier et al., as well as others, have been concerned with obtaining addition products from the reaction of aliphatically unsaturated compounds and silicon compounds having silicon-bonded-hydrogen atoms. However, none have suggested that there are situations where the product of such a reaction is an inhibitor for the very reaction by which it is made. Thus, the reaction begins but as soon as a small amount of product is produced the reaction stops because the products inhibit the reaction by poisoning the catalyst. The present invention is directed to a preparation of a unique class of compounds which inhibit the catalyst at low temperatures but not at high temperatures. Because the catalyst which is inhibited is used to make the inhibiting compound, the preparation method to provide a commercially suitable process was not obvious. The inhibiting compounds are a class of siloxane compounds containing olefinic unsaturation and are prepared from acetylenic alcohols and siloxane compounds having silicon-bonded-hydrogen atoms. The earliest work did not produce an inhibiting compound for the platinum catalyzed addition of aliphatic unsaturation to silicon-bonded hydrogen, but instead provided a complex mixture which may be called "a crosslinker-catalyst-inhibitor." This work is the subject of a copending application Ser. No. 528,962 filed Dec. 2, 1974 entitled "Crosslinker-platinum Catalyst-Inhibitor and Method of Preparation Thereof" by Randolph G. Niemi filed on even date herewith and assigned to the same party. Niemi combined polysiloxane having multiple silicon-bonded hydrogen atoms, a platinum catalyst and an acetylenic alcohol, heated the mixture for about 16 hours to 70°C. and obtained a complex mixture after removing unreacted acetylenic alcohol by reduced pressure at room temperature, which when mixed with vinyl containing siloxane polymers remained uncured at room temperature but would cure at elevated temperatures. Thus, Niemi had found one could make room temperature stable compositions from his mixture, but for each composition a separate mixture of crosslinker, catalyst and acetylenic alcohol was required. Attempts to separate the complex mixture into various components were impractical and expensive. The product could not be characterized to identify any particular species which was responsible for the inhibiting effects on platinum catalysts.

Using the method of Niemi, Chi-Long Lee and Ollie W. Marko as described in a copending application Ser. No. 528,966 filed Dec. 2, 1974 entitled "Olefinic Siloxanes As Platinum Inhibitors" filed on even date herewith and assigned to the same party prepared specific olefinic siloxane compounds which were inhibitors for the platinum catalysts in the addition reaction between aliphatic unsaturation and silicon-bonded hydrogen atoms. For example, Lee and Marko mixed equal molar quantities of (I) 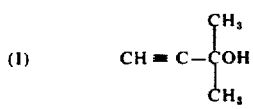

and (II)     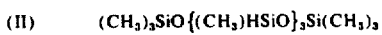

with a catalytic amount of a platinum catalyst from 2 to 50 parts per million platinum, heated the mixture at 70°C. for 16 hours, stripped off the unreacted starting ingredients, let set over night and then vacuum distillation was used to recover the product. The product was an olefinic siloxane compound of the formula

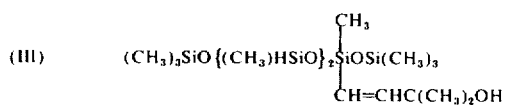

(III)     (CH₃)₃SiO{(CH₃)HSiO}₂SiOSi(CH₃)₃
              CH=CHC(CH₃)₂OH

This compound mixed with a vinylsiloxane polymer, a silicon-bonded nitrogen containing compound and a platinum catalyst did not cure at room temperature in 10 days but when heated to 150°C. the composition cured in two minutes. Thus, this compound is a platinum catalyst inhibitor at room temperature, but not at elevated temperature.

Although Lee and Marko were able to characterize specific inhibitor compounds, the method of preparation was impractical. The process provided only a low conversion from 2 to 20 percent and the yield was less than 5 percent after distillation. In addition to both low conversion and yield, the reaction was difficult to control and could become violently exothermic, thus creating a safety hazard.

To improve the process, Lee and Marko discovered that the inhibitor could be prepared in a gas liquid chromatographic column as described in a copending application Ser. No. 528,959, filed Dec. 2, 1974 entitled "Method of Preparing Olefinic Siloxane By GLC" filed on even date herewith and assigned to the same party. Lee and Marko coated the injection port of a GLC column with a layer of platinum catalyst, heated the port at 350°C. and injected a mixture of (I) and (II) while maintaining the column at 300° to 400°C. The product (III) was obtained in yields of from 30 to 35 percent. This process had advantages over the Niemi process in that less platinum catalyst was used, very short residence times down to 1 to 2 seconds were needed, the yields were higher, high purity product was obtained and separate distillations were not needed. However, the method was not suitable for the production of large amounts of olefinic siloxane inhibitor. When larger GLC columns were used the yields decreased and the column became plugged by gelled materials. Thus, for small scale operations this methohd was found suitable but was deficient for large scale production.

Another process developed to make the olefinic siloxane compound inhibitors is described in a copending application Ser. No. 528,960, filed Dec. 2, 1974 entitled "Tube Method For The Preparation Of Olefinic Siloxane Compounds" by Chi-Long Lee and Myron T. Maxson, filed on even date herewith and assigned to the same party. In this method a heated tube is used, the starting ingredients are injected into the heated tube using a carrier gas such as helium, passed through the tube and then the products are condensed either by a single condenser or by multiple condensers in series at different temperatures. This process combines (I), (II) and a platinum catalyst, injects the mixture in a helium gas carrier into the tube at a temperature of 300° to 400°C. The residence time in the tube can be varied from about 20 seconds to one minute or more. The reaction product is condensed as it exits from the reactor. If a single condenser is used, the product mixture is distilled to recover (III). If multiple condensers are used, each condenser is at a different temperature and the separation of (III) from unreacted species is immediately obtained. With this method, yields of (III) up to 60 percent were obtained. Although the yields were considerably higher than the other methods, the tube did become plugged during long, continuous use and the temperature were high and considerable decomposition of materials was observed.

From the methods described above, the desired products can be prepared but each have disadvantages which do not lend themselves to ready commercial processes and although these methods have value they were not the best method. Another method to produce the olefinic siloxane compound inhibitor has now been developed which is the basis for this invention.

SUMMARY OF THE INVENTION

An object of this invention is to provide a method for preparing an olefinic siloxane compound which is an inhibitor for platinum at room temperature and which is not an inhibitor at elevated temperatures.

This invention relates to a method for preparing olefinic siloxane compounds by heating in the presence of a platinum catalyst a mixture of acetylenic alcohol and siloxane compound having at least three silicon-bonded hydrogen atoms bonded to separate silicon atoms above 100°C. and above the temperature at which the olefinic siloxane product is an inhibitor for the reaction and at a pressure sufficient to keep the starting ingredients and product in a liquid phase at least until they have passed through a heating means. The product obtained is an olefinic siloxane which inhibits the reaction between aliphatic unsaturated compounds and silicon-bonded hydrogen atoms catalyzed by a platinum catalyst at room temperature but allows the reaction to occur at elevated temperatures.

DESCRIPTION OF THE INVENTION

This invention relates to a method of reacting an acetylenic alcohol with a siloxane compound having at least three silicon-bonded-hydrogen atoms bonded to at least three different silicon atoms in the presence of a platinum catalyst to provide an olefinic siloxane compound wherein the olefinic siloxane compound is an inhibitor for the platinum catalyst comprising continuously passing a liquid mixture of the acetylenic alcohol and the siloxane compound having at least three silicon-bonded-hydrogen atoms in the presence of a platinum catalyst through a heating means wherein the liquid mixture is heated to a temperature which is above 100°C. and which is also above the temperature at which the olefinic siloxane compound is no longer an inhibitor for the reaction, but the temperature and residence time of the liquid mixture in the heating means being sufficient to produce the olefinic siloxane compound without substantial decomposition of reactants and product, said liquid mixture is under sufficient pressure to maintain the reactants and product in a liquid state at least until the mixture has passed through the heating means, said product being an olefinic siloxane compound which is, below 100°C., an inhibitor for the reaction between the acetylenic alcohol and the siloxane compound having at least three silicon-bonded-hydrogen atoms in the presence of a platinum catalyst.

The method of this invention is a continuous method wherein the reactants are continuously fed into a closed system and the product is continuously removed. The desired amounts of acetylenic alcohol, platinum catalyst and siloxane having silicon-bonded hydrogen atoms are either premixed or separately metered and thoroughly mixed just before going into the heating means. The reactants can be neat or in an inert solvent. The platinum catalyst is preferably mixed with at least one of the reactants to better control the amount used and to guarantee a thorough distribution of catalyst in the reactants. The reactants are most conveniently premixed before entering the closed system.

The reactants are pumped into a heating means at a rate to provide a residence time in the heating means to provide sufficient product. This residence time can vary from a few seconds up to about one hour. The particular residence time in the heating means will be dependent on the temperature of the heating means, the platinum catalyst concentration and the yield of product with which one is satisfied. At any given temperature and platinum catalyst concentration, the yield will increase with longer residence times. Higher temperatures and higher platinum catalyst concentrations will also increase the yield of product. The heating means is not critical in design or manner of operation as long as the reactants can be provided with a certain specified residence time, pressure and temperature. Such a heating means can be a coiled or straight tube running through a bath which can be controlled as to temperature. The tube is of sufficient length to permit variation in residence time as controlled by the pumping capabilities. If a bath were used to heat the reaction chamber, the bath temperature should be sufficient to heat the reactants to the desired reaction temperatures during the residence time.

The reaction temperature must be above 100°C. and also above the temperature at which the product is an inhibitor for the reaction catalyst. The maximum temperature is dependent upon the residence time and the amount of decomposition which one considers tolerable. Preferably reaction temperatures do not provide any decomposition of reactants or product. The reaction temperature which provides the optimum results will depend upon the particular reactants and platinum catalyst concentration. The minimum temperature required will be determined by the strength of the resulting product to inhibit the platinum catalyst, but will be above 100°C. under any circumstances, because the reaction would not produce any useful product in reasonable yield below this temperature. Therefore, if the product, which is the inhibitor, inhibits up to 125°C., the reaction temperature will need to be above 125°C. The temperature range for this reaction is most useful from 150°C. to about 400°C.

The residence time of the reaction mixture will depend upon the temperature of the heating means, the platinum catalyst concentration, the amount of product yield acceptable and the level of decomposition which is tolerable. The residence times of from 5 seconds to 30 minutes are preferred, with excellent results being obtainable with residence times of 5 to 60 seconds.

The reacted mixture is cooled as it leaves the heating means and the product is separated from any unreacted starting materials. The reaction product can be distilled to recover the starting materials which are recycled and the product can be distilled into fractions if necessary or desired. However, the product is useful as obtained, once the starting ingredients are removed and separation is not really necessary to have a useful inhibitor.

The above reaction is done in a system which can be pressurized. The amount of pressure required will be determined by the volatility of the reactants because the reaction mixture is required to remain a liquid at least through the heating means. The pressure can vary widely and is not critical within any particular limits except as to that amount sufficient to keep the reactants in the liquid state and the amount of pressure which the particular equipment will tolerate, such as up to 1000 pounds per square inch (70.3 kilograms per square centimeter). A range of from 50 to 450 pounds per square inch (3.5 to 31.6 kilograms per square centimeter) have been found to be convenient to provide useful results.

The acetylenic alcohol can be any of those alcohols having a C ≡ C bond which when reacted with a siloxane compound having SiH results in an olefinic containing siloxane which are inhibitors for platinum catalyst at room temperature but not at elevated temperatures above 100°C. Examples of such acetylenic alcohols, include, 3-methyl-1-butyn-3-ol, 1-ethynylcyclohexan-1-ol, 3,5-dimethyl-1-hexyn-3-ol, 3-methyl-1-pentyn-3-ol and the like.

The siloxane compounds are those having at least three silicon-bonded hydrogen atoms bonded to at least three separate silicon atoms. These siloxane compounds can be straight chain, cyclic, or branched. These siloxanes can be copolymers, homopolymers, single species, mixtures of the various types mentioned above. It is preferred that these siloxane compounds have at least two silicon-bonded hydrogen atoms bonded to silicon atoms separated by one oxygen atom, preferably three silicon-bonded hydrogen atoms bonded to three silicon atoms which are only separated by oxygen. Some of the siloxane compounds for use in the present method are defined by the following generic formulae, R₃SiO(RHSiO)ₓSiR₃,   HR₂SiO(RHSiO)ᵤSiR₂H,
(RHSiO)ᵥ,
HR₂SiO(RHSiO)ᵤ(R₂SiO)ₓSiR₂H,
R₃SiO(R₂SiO)ₓ(RHSiO)ₓSiR₃,   HR₂SiO(RHSiO)ᵣSiR₃,
HR₂SiO(R₂SiO)ₓ(RHSiO)ᵣSiR₃,

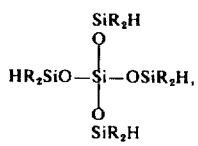

and the like, wherein each R is a monovalent hydrocarbon radical having no aliphatic unsaturation such as methyl, ethyl, phenyl, propyl, hexyl, cyclohexyl, octyl, dodecyl, cyclopentyl, isopropyl, or fluorinated monovalent hydrocarbon radicals such as 3,3,3-trifluoropropyl, other perfluoroalkylethyl radicals, α,α,α-trifluoromethylphenyl, hexafluorophenyl and the like. The number of siloxane units per molecule can vary from as little as 3 to any number which can be pumped through the system, preferably from 3 to 50 siloxane units per molecule. Other siloxane compounds are also suitable such as those which have arylene or alkylene bonds between some of the silicon atoms. Some specific siloxane compounds include

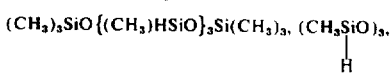

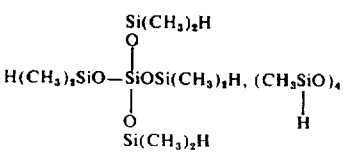

and the like.

The platinum catalyst is not narrowly critical and can be chloroplatinic acid, platinum chlorides, platinum salts, platinum deposited on a solid carrier such as silica, charcoal, or alumina, platinous halide complexes with olefins and other well known platinum catalysts. These and other platinum catalyst are further defined and illustrated in U.S. Pat. No. 3,453,234, issued July 1, 1969 to Gust J. Kookootsedes, and hereby included by reference to illustrate platinum catalyst.

The amount of acetylenic alcohol and siloxane compound having silicon-bonded hydrogen atom can vary broadly. Molar ratios of one to one have been found suitable, however, the ratio of acetylenic alcohol to siloxane compound can preferably be varied from 10/1 to 1/10 and still obtain product. Wherein ratios of less than 1/1 are used the amount of product obtained even at 100 percent conversion will be less than obtainable when a 1/1 ratio is used, however, an amount of monoadduct is increased compound to di-adduct and multiadduct.

The amount of platinum catalyst is not narrowly critical for the lower limit as long as a sufficient amount is present to catalyze the reaction. Amounts in the order of 0.05 parts by weight platinum per one million parts by weight of acetylenic alcohol and siloxane compound are suitable. The maximum amount is determined by the amount which will cause undesirable amounts of decomposition. This maximum amount will depend upon the type of siloxane compound, acetylenic alcohol and platinum catalyst, as well as the temperature of reaction. Generally, less platinum catalyst is required the higher the reaction temperature. For most reactions amounts from 0.1 to 2 parts per million platinum can be used, but caution should be taken to prevent decomposition at the higher concentrations. One advantage of this method is the ability to control the reaction and minimize violent exotherms.

The method of this invention produces an olefinic siloxane compound which is the addition product of the acetylenic alcohol and the siloxane compound having at least three silicon-bonded hydrogen atoms. The addition products, which are produced in major amounts and which are the inhibitors, are those which do not add to all the silicon-bonded hydrogen atoms. There should be at least one unreacted silicon-bonded hydrogen bond per molecule of olefinic siloxane compound. The method of this invention provides addition products, which are inhibitors, in amounts of greater than 80 percent combined mono-adducts and di-adducts. Both the mono- and di-adducts are inhibitors, however, when all the silicon-bonded hydrogen atoms are reacted the product is markedly reduced in inhibition activity.

The olefinic siloxane compound inhibitors are useful in that these compounds retard the room temperature reaction of vinyl compounds with silicon-bonded hydrogen atoms which are catalyzed with platinum but allow the reaction to occur rapidly at elevated temperature such as at 150°C. Thus, these olefinic siloxane compounds can be used to make one package compositions which cure on heating but are stable over extended periods of time at ambient conditions.

The following examples are presented for illustrative purposes and should not be construed as limiting the invention which is properly delineated in the appended claims.

EXAMPLE 1

A mixture was prepared by combining the acetylenic alcohol identified above by formula (I), the siloxane identified above by formula (II) and a platinum catalyst complex of chloroplatinic acid hexahydrate and 1,3-divinyl-1,1,3,3-tetramethyldisiloxane containing 0.63 weight percent platinum. The mixture contained 10 moles of (I) to one mole of (II) with the amount of platinum catalyst as defined in Table A reported as parts by weight platinum per one million parts by weight (I) and (II) (ppm). A closed system with pressurizing equipment, a heating bath with coil through which the liquid reaction mixture was passed, a cooling unit and appropriate pressure and temperature indicators was used. A polydimethylsiloxane fluid having a viscosity of one centistoke was pumped through the system until the operating conditions were reached, including temperature, pressure and residence time in the heating unit. The mixture was then pumped into the system continuously to provide a residence time of six minutes in the heating bath. The temperature of the stream was measured at the point where the coil left the heating bath and was as shown in Table A. The reacted mixture was continuously collected after being cooled. The product was identified by mass spectroscopy and nuclear magnetic resonance and quantities determined by GLC and the various species and amounts were as shown in Table A. The "% Conversion" as shown in Table A was determined by integrating the area under the GLC curve and the sum of the areas for the monoadduct, di-adduct, tri-adduct divided by the sum of the areas for the mono-adduct, di-adduct, tri-adduct and unreacted siloxane (II) and then multiplied by 100 gave the percent conversion as reported herein. The area under the GLC curve are directly related to the weight of ingredient in the mixture and thus the percent conversion provided a means of evaluating the experiments. The adducts were as follows wherein the formulae shown are for illustrative purposes and do not indicate the exact position of all the olefinic radicals in the molecule for each adduct. There will be mixtures of different structural isomers for the mono and di adducts present, Mono-adduct (III) 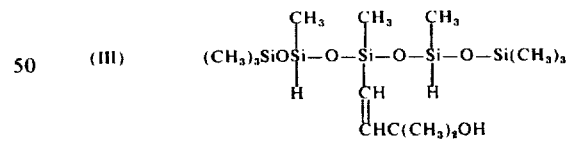

Di-adduct (IV) 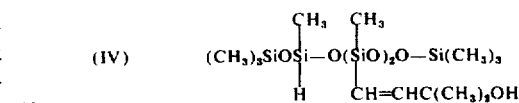

Tri-adduct (V) 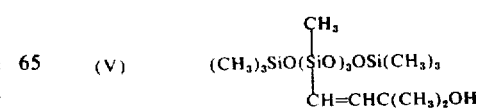

Table C

| Run No. | Moles of (I) | Temperature, °C. | Pressure, Kg/cm² | % Conversion | % Adduct | % Mono-Adduct | % Di-Adduct | % Tri-Adduct, % | Total of Mono and Di |
| --- | --- | --- | --- | --- | --- | --- | --- | --- | --- |
| 1 | 1.0 | 189 | 5.48 (78 p.s.i.) | 28.4 | 53.9 | 40.5 | 5.6 | 94.4 | |
| 2 | 1.0 | 189 | 8.79 (125 p.s.i.) | 27.9 | 54.5 | 39.4 | 6.1 | 93.9 | |
| 3 | 1.0 | 192 | 15.82 (225 p.s.i.) | 37.1 | 48.7 | 41.9 | 9.4 | 90.6 | |
| 4 | 0.8 | 189 | 5.34 (76 p.s.i.) | 25.1 | 53.4 | 36.3 | 10.3 | 89.7 | |
| 5 | 0.8 | 189 | 8.79 | 24.7 | 55.1 | 37.2 | 7.7 | 92.3 | |
| 6 | 0.8 | 194 | 15.82 | 29.2 | 53.2 | 39.0 | 7.8 | 92.2 | |
| 7 | 0.6 | 179 | 5.62 (80 p.s.i.) | 17.0 | 62.4 | 32.9 | 4.7 | 95.3 | |
| 8 | 0.6 | 181 | 15.82 | 18.4 | 62.0 | 32.6 | 5.4 | 94.6 | |
| 9* | 0.4 | 182 | 5.27 (75 p.s.i.) | 18.2 | 65.4 | 29.1 | 5.5 | 94.5 | |
| 10 | 0.4 | 191 | 15.82 | 13.3 | 64.9 | 26.8 | — | 91.7 | |

*Residence time was 6.12 minutes.

The amount of mono-adduct and di-adduct in the reaction product represented by the percent conversion was as shown in Table A by the weight percentages. The sum of the weight percentages of the mono-adduct and the di-adduct is indicated in Table A as the total amount of polyorganosiloxane which was useful as an inhibitor for platinum catalyst.

Table A

| Run No. | Platinum, ppm | Temperature, °C. | Pressure, Kg/cm² | % Conversion | % Mono-Adduct | % Di-Adduct | Total of Mono and Di adduct, % |
| --- | --- | --- | --- | --- | --- | --- | --- |
| 1 | 0 | 160 | 14.06 (200 p.s.i.) | 0 | 0 | 0 | 0 |
| 2 | 0.25 | 160 | 14.06 | 1.7 | 55.5 | 42.0 | 97.5 |
| 3 | 0.50 | 160 | 14.06 | 7.3 | 51.5 | 42.0 | 93.5 |
| 4 | 0.75 | 160 | 14.06 | 12.4 | 51.3 | 44.2 | 95.5 |
| 5 | 1.00 | 160 | 14.06 | 20.0 | 37.5 | 62.5 | 100.0 |
| 6 | 2.00 | 160 | 14.06 | 35.6 | 38.2 | 59.0 | 97.2 |
| 7 | 0.25 | 194 | 15.82 (225 p.s.i.) | 28.8 | 49.0 | 50.0 | 99.0 |
| 8 | 0.50 | 194 | 15.82 | 50.5 | 40.0 | 51.0 | 91.0 |
| 9 | 0.75 | 197 | 15.82 | 58.0 | 38.4 | 53.0 | 91.4 |
| 10 | 1.00 | 195 | 15.82 | 75.5 | 24.5 | 59.0 | 83.5 |
| 11 | 2.00 | 193 | 15.82 | 92.6 | 18.4 | 58.6 | 77.0 |

EXAMPLE 2

The method of Example 1 was followed using a platinum catalyst level of 1.0 ppm. platinum, a pressure of 15.82 kilograms per square centimeter, and a temperature of 190°C. to 196°C. as shown in Table B. The amounts of (I) and (II) were varied as described in Table B where (II) was kept at one mole while varying the amount of (I). The results were as shown in Table B which show that the percentage conversion was directly related to the mole ratio of acetylenic alcohol (I) to siloxane (II).

EXAMPLE 3

The method of Example 1 was followed using a platinum catalyst level of 1.0 ppm. platinum, a residence time of 6 minutes, and a temperature and pressure as shown in Table C. The amounts of (I) and (II) were varied as described in Table C where (II) was kept at one mole while varying the amount of (I).

EXAMPLE 4

The method of Example 1 was followed using 0.125 ppm. platinum, 0.8 mole (I) and one mole of (II) and a temperature, pressure and residence time as described in Table D. The results were as shown in Table D which show variations of residence time. Table D also shows that residence time influenced the percent conversion and that above 200°C. the amount of decomposition found was interrelated to residence time, temperature and pressure. The percent decomposition was the weight of material unaccounted for and not one of the Table B

| Run No. | Moles of (I) | Temperature, °C. | % Conversion | % Mono-Adduct | % Di-Adduct | % Tri-Adduct | Total of Mono and Di Adduct, % |
| --- | --- | --- | --- | --- | --- | --- | --- |
| 1 | 10.00 | 195 | 75.5 | 24.5 | 59.0 | 16.5 | 83.5 |
| 2 | 1.25 | 196 | 45.0 | 45.2 | 44.4 | — | 89.6 |
| 3 | 1.00 | 192 | 37.1 | 48.7 | 41.9 | 9.4 | 90.6 |
| 4 | 0.80 | 194 | 29.2 | 53.2 | 39.0 | 7.8 | 92.2 |
| 5 | 0.60 | 192 | 22.6 | 57.0 | 35.1 | — | 92.1 |
| 6 | 0.40 | 191 | 13.3 | 64.9 | 26.8 | — | 91.7 |
| 7 | 0.20 | 190 | 7.6 | 75.0 | 23.0 | 2.0 | 98.0 |
| 8 | 0.10 | 190 | 5.0 | 83.0 | 16.0 | 1.0 | 99.0 | starting ingredients or adducts divided by the total weight of material multiplied by 100.

The 3-methyl-1-pentyn-3-ol and (II) resulted in a 47 percent conversion with 54 percent being the mono- Table D

| Run No. | Residence Time, sec. | Temperature, °C. | Pressure, Kg/cm² | % Conversion | % Mono-Adduct | %Di-Adduct | % Tri-Adduct | Total of Mono and Di-Adduct, % | % Decomposition |
|---|---|---|---|---|---|---|---|---|---|
| 1 | 419 | 300 | 21.09 (300 p.s.i.) | 38.5 | 60.8 | 34.3 | 4.9 | 95.1 | 2.5 |
| 2 | 360 | 288 | 12.30 (175 p.s.i.) | 31.8 | 60.7 | 36.2 | 3.1 | 96.9 | 4.9 |
| 3 | 198 | 292 | 21.09 | 32.5 | 65.5 | 33.9 | 0.6 | 99.4 | 14.2 |
| 4 | 180 | 308 | 21.09 | 29.3 | 62.1 | 34.1 | 3.8 | 96.4 | 0.3 |
| 5 | 99 | 300 | 28.12 (400 p.s.i.) | 35.9 | 57.9 | 36.8 | 5.3 | 94.7 | 6.5 |
| 6 | 36.3 | 298 | 28.12 | 43.1 | 56.3 | 36.5 | 7.2 | 92.8 | <1 |
| 7 | 31.3 | 300 | 21.09 | 18.7 | 61.0 | 38.0 | 1.0 | 99.0 | — |
| 8 | 28.9 | 300 | 28.12 | 43.8 | 61.7 | 34.5 | 3.8 | 96.2 | 1 |
| 9 | 27.4 | 291 | 21.09 | 12.0 | 65.8 | 32.5 | 1.7 | 98.3 | — |
| 10 | 23.5 | 305 | 28.12 | 42.8 | 58.3 | 37.9 | 3.8 | 96.2 | 5.7 |
| 11 | 15.5 | 300 | 28.12 | 33.3 | 63.1 | 34.8 | 2.1 | 97.9 | 0.8 |
| 12 | 14.9 | 309 | 28.12 | 38.1 | 63.5 | 32.8 | 3.7 | 96.3 | 1.9 |
| 13 | 14.9 | 290 | 29.88 (425 p.s.i.) | 21.3 | 64.3 | 33.8 | 1.9 | 98.1 | — |
| 14 | 14.6 | 290 | 29.88 | 32.9 | 60.2 | 34.0 | 5.8 | 94.2 | — |
| 15 | 13.5 | 298 | 28.12 | 15.2 | 62.5 | 36.2 | 1.3 | 98.7 | 1.6 |

EXAMPLE 5

The method of Example 1 was followed using 2.5 moles of (I) to one mole of (II), a platinum catalyst in the amount of 2 ppm. platinum, a temperature of 160°C., a pressure of 14.06 kilograms per square centimeter and the residence times were varied 6 minutes, 9 minutes, 12 minutes and 18 minutes. The conversion percentages were 24.1, 31.2, 37.7 and 49.6 respectively.

EXAMPLE 6

The method of Example 1 was followed using platinum catalyst in the amount of 2 ppm. platinum, a temperature of 190° to 192°C., a pressure of 16.87 kilograms per square centimeter (240 p.s.i.) and a residence time of 6 minutes. Two experiments were run, one using 3,5-dimethyl-1-hexyn-3-ol and the other using 3-methyl-1-pentyn-3-ol. The acetylenic alcohols were used in amounts of one mole of alcohol to one mole of (II).

The 3,5-dimethyl-1-hexyn-3-ol and (II) resulted in a 52 percent conversion with 52 percent being the mono-adduct having two trimethylsiloxy units, two methylhydrogensiloxane units and one siloxane unit of the formula

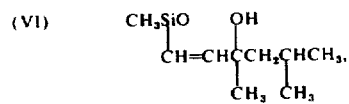

(VI)

42 percent being the di-adduct having two trimethylsiloxy units, one methylhydrogensiloxane unit and two siloxane units of formula (VI) and 5% being the tri-adduct having two trimethylsiloxy units and three siloxane units of formula (VI).

adduct having two trimethylsiloxy units, two methylhydrogensiloxane units and one unit of the formula

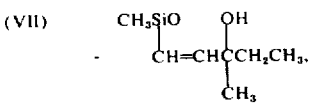

(VII)

38 percent being the di-adduct having two trimethylsiloxy units, one methylhydrogensiloxane unit and two siloxane units of formula (VII), and 7 percent being tri-adduct having two trimethylsiloxy units and three siloxane units of formula (VII).

EXAMPLE 7

Compositions were prepared by mixing 63 parts by weight of phenylmethylvinylsiloxy endblocked polydimethylsiloxane having a viscosity of about 400 centistokes at 25°C., 33 parts by weight 5 micron quartz, 4.87 parts by weight of trimethylsiloxy endblocked polyorganosiloxane having an average of 10 silicon atoms per molecule, an average of three dimethylsiloxane units per molecule and an average of five methylhydrogensiloxane units per molecule, 12 parts by weight platinum per one million parts by weight composition where the platinum was in the form of a complex platinum catalyst prepared from chloroplatinic acid hexahydrate and symetrical divinyltetramethyldisiloxane having about 0.65 weight percent platinum and the amount of adduct as defined in Table E by the formulae identified in Example 1. Single species adducts were obtained by distillation of the reaction product of Example 4, Run No. 8. The results were as shown in Table E where the cure times were obtained at various temperatures. the cure times were the times required at a given temperature for the composition to become a cured elastomer.

Table E

| Curable Composition Reference | Adduct Formula | Amount Adduct | Cure Times | | | |
|---|---|---|---|---|---|---|
| | | | at 150°C. minutes | at 100°C. minutes | at 50°C. hours | RT days |
| A. | (III) | 0.0016 mole | 3 | <10 | 3-4 | 6 |
| B. | (III) | 0.0032 mole | 3 | 10 | >6 | 14 |
| C. | (IV) | 0.0016 mole | 3.5 | <10 | >6 | 18 |
| D. | (IV) | 0.0032 mole | 4 | 13 | 8-24 | 63 |

Table E-continued

| Curable Composition Reference | Adduct Formula | Amount Adduct | Cure Times at 150°C. minutes | at 100°C. minutes | at 50°C. hours | RT days |
|---|---|---|---|---|---|---|
| E. | 85% (IV), 15% (V)** | 0.0016 mole | 3.5 | <10 | >6 | 16 |
| F. | 85% (IV), 15% (V)** | 0.0032 mole | 4.5 | 13 | 8-24 | 50 |
| G. | (V) | 0.0016 mole | 2.5 | <10 | 2 | 1.2 |
| H. | (V) | 0.0032 mole | 3 | 10 | 3.5 | 6 |
| I. | 56% (III), 33% (IV), 5% (V)*** | 2%*** | — | — | — | S108 |
| J. | 56% (III), 33% (IV), 5% (V)*** | 4%*** | — | — | — | S108 |
| K. | (III) | 2%*** | — | — | — | S108 |
| L. | (III) | 2%*** | — | — | — | S108 |

**Percent is mole percent.
***Percent is weight percent.

That which is claimed is:

1. A method of reacting an acetylenic alcohol with a siloxane compound having at least three silicon-bonded-hydrogen atoms bonded to at least three different silicon atoms in the presence of a platinum catalyst to provide an olefinic siloxane compound wherein the olefinic siloxane compound is an inhibitor for the platinum catalyst comprising continuously passing a liquid mixture of the acetylenic alcohol and the siloxane compound having at least three silicon-bonded-hydrogen atoms in the presence of a platinum catalyst through a heating means wherein the liquid mixture is heated to a temperature which is above 100°C. and which is also above the temperature at which the olefinic siloxane compound is no longer an inhibitor for the reaction, but the temperature and residence time of the liquid mixture in the heating means being sufficient to produce the olefinic siloxane compound without substantial decomposition of reactants and product, said liquid mixture is under sufficient pressure to maintain the reactants and product in a liquid state at least until the mixture has passed through the heating means, said product being an olefinic siloxane compound which is, below 100°C., an inhibitor for the reaction between the acetylenic alcohol and the siloxane compound having at least three silicon-bonded-hydrogen atoms in the presence of a platinum catalyst.

2. The method in accordance with claim 1 in which the residence time is from 5 seconds to one hour, the liquid mixture is heated to a temperature in the range from 150°C. to 400°c., at a pressure in the range of 3.5 to 70.3 kilograms per square centimeter and the platinum catalyst is present in an amount of from 0.05 to 2 parts by weight platinum per one million parts by weight of acetylenic alcohol and siloxane compound having at least three silicon-bonded-hydrogen atoms.

3. The method in accordance with claim 1 in which the acetylenic alcohol is 3-methyl-1-butyn-3-ol.

4. The method in accordance with claim 1 in which any unreacted acetylenic alcohol and siloxane compound having at least three silicon-bonded-hydrogen atoms are removed from the olefinic siloxane compound by distillation.

5. The method in accordance with claim 2 in which any unreacted acetylenic alcohol and siloxane compound having at least three silicon-bonded-hydrogen atoms are removed from the olefinic siloxane compound by distillation.

6. The method in accordance with claim 3 in which any unreacted 3-methyl-1-butyn-3-ol and siloxane compound having at least three silicon-bonded hydrogen atoms are removed from the olefinic siloxane compound by distillation.

7. The method in accordance with claim 3 in which the siloxane compound having at least three silicon-bonded hydrogen atoms is an organosiloxane having two $(CH_3)_3SiO_{0.5}$ units and three $(CH_3)HSiO$ units wherein the mixture is heated to a temperature between 160°C. and 350°C. at a pressure of 14.1 to 70.3 kilograms per square centimeter.

* * * * *